United States Patent
Ganesh et al.

(10) Patent No.: US 7,278,420 B2
(45) Date of Patent: Oct. 9, 2007

(54) OROPHARYNGEAL AIRWAY

(75) Inventors: Arjunan Ganesh, Bryn Mawr, PA (US); Valerie E. Armstead, Moorestown, NJ (US); Michael J. Williams, Moorestown, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 10/666,290

(22) Filed: Sep. 19, 2003

(65) Prior Publication Data
US 2004/0129272 A1 Jul. 8, 2004

Related U.S. Application Data

(60) Provisional application No. 60/413,174, filed on Sep. 24, 2002.

(51) Int. Cl.
*A61M 16/08* (2006.01)

(52) U.S. Cl. .................. 128/200.26; 128/207.14; 128/207.18

(58) Field of Classification Search .......... 128/200.26, 128/204.18, 205.25, 207.15, 859, 207.14, 128/207.16, 201.25, 911, 203.22; 600/194, 600/202, 205; 606/108, 280
See application file for complete search history.

(56) References Cited

U.S. PATENT DOCUMENTS

| | | | |
|---|---|---|---|
| 2,127,215 A * | 8/1938 | Gwathmey | 128/207.14 |
| 3,756,244 A * | 9/1973 | Kinnear et al. | 128/207.14 |
| 3,908,665 A * | 9/1975 | Moses | 128/207.14 |
| 4,198,970 A | 4/1980 | Luomanen | 128/207.15 |
| 4,231,365 A * | 11/1980 | Scarberry | 128/207.15 |
| 4,821,715 A * | 4/1989 | Downing | 128/207.18 |
| 5,024,218 A | 6/1991 | Ovassapian et al. | 128/200.26 |
| 5,582,167 A | 12/1996 | Joseph | 128/207.15 |
| 5,653,229 A | 8/1997 | Greenberg | 128/207.15 |
| 5,776,052 A | 7/1998 | Callahan | 600/194 |
| 5,819,723 A | 10/1998 | Joseph | 128/207.14 |
| 5,976,072 A * | 11/1999 | Greenberg | 600/12 |
| 6,098,617 A * | 8/2000 | Connell | 128/200.26 |
| 6,256,524 B1 | 7/2001 | Walker et al. | 600/340 |
| 6,568,388 B2 * | 5/2003 | Christopher | 128/200.26 |
| 2002/0108610 A1 * | 8/2002 | Christopher | 128/200.26 |

* cited by examiner

*Primary Examiner*—Justine R. Yu
*Assistant Examiner*—Shumaya B. Ali
(74) *Attorney, Agent, or Firm*—Paul & Paul

(57) ABSTRACT

An oropharyngeal device for insertion into the mouth of a patient. The device includes a body having a distal end and a proximal end with a flange formed at the proximal end. The distal end is inserted into the mouth until the flange is disposed outside and adjacent to the patient's mouth. The flange keeps the proximal device from entering the mouth. The body is sized such that the distal end of the body is disposed within the pharynx above the epiglottis. The device includes a channel that forms an airway between the ends. The device also includes at least three separate conduits integrated into the body for administering oxygen, suctioning, and for assessing ventilation thorough end-tidal carbon dioxide monitoring. The conduits for oxygenation and suctioning extend through the body between its proximal and distal ends. The conduit for end-tidal carbon dioxide monitoring terminates within the channel.

15 Claims, 6 Drawing Sheets

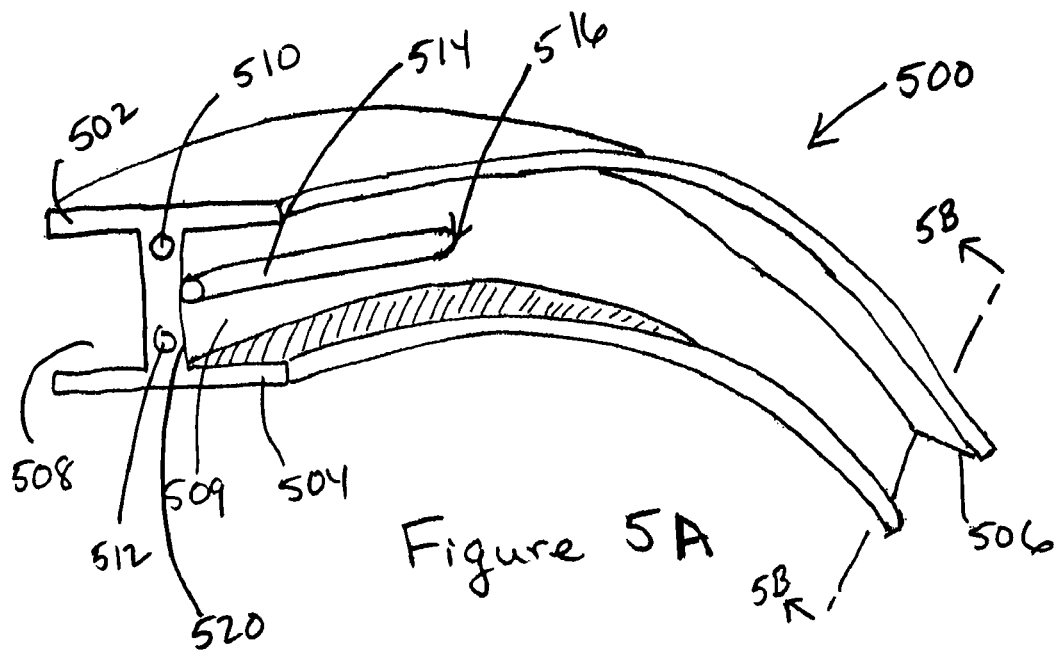
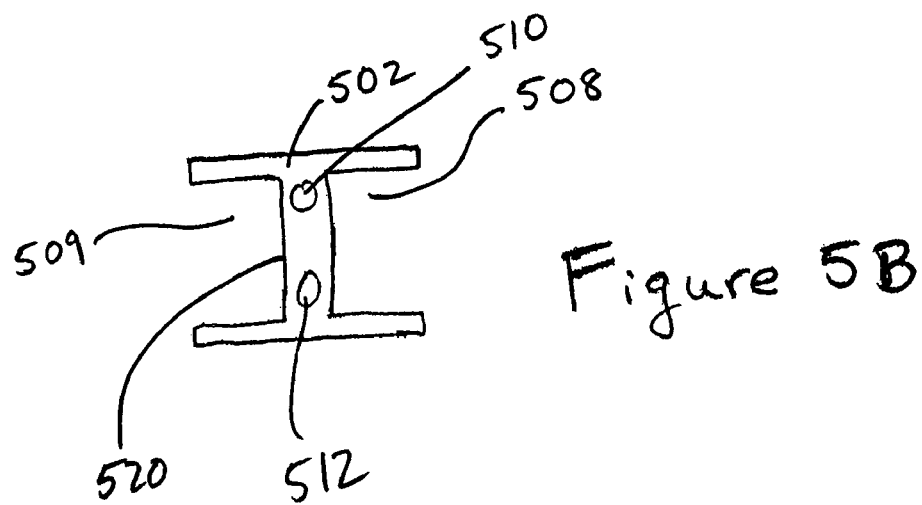

OROPHARYNGEAL AIRWAY

CROSS-REFERENCE TO RELATED APPLICATION

The present invention is related to and claims priority from now abandoned U.S. Provisional Patent Application Ser. No. 60/413,174, filed Sep. 24, 2002, incorporated by reference in its entirety.

FIELD OF THE INVENTION

The invention relates to establishing and maintaining an airway and, in particular, to an oropharyngeal device for establishing and maintaining an airway.

BACKGROUND OF THE INVENTION

The administration of anesthesia via a face mask technique usually requires continuous hands-on management. This is inconvenient during certain medical procedures that require access to the face because the face mask technique may obstruct access to the face.

For example, access to the face may be necessary for ophthalmologic examination, radiation therapy, MRIs (magnetic resonance imaging), and CT (computed tomography) or CAT (computed axial tomography) scans. If a mask is used to administer anesthesia during such procedures, access the patient's face may be hindered. Further, in such circumstances, anesthesiologists often use awkward hand positioning to allow access to the face which then requires repeated manipulation of the mask to ensure a patent airway.

The administration of anesthesia via a face mask technique is also inconvenient when the anesthesiologist must be distant from the patient such as during radiation therapy, CT or CAT scans, and during MRIs. Although the anesthesiologist may repeatedly instrument the trachea in such circumstances, the stimulation may result in irritation of the trachea especially when treatment is necessary on an on-going basis. For example, during radiation therapy, patients may be repeatedly treated each day over a period of several weeks. Repeated instrumentation during this on-going treatment will irritate the patient's trachea and may result in other adverse consequences such as a sore throat and loss of appetite due to the irritated trachea and hypopharynx.

The above situations are conventionally resolved by using general anesthesia with endotracheal intubation, by using intravenous techniques without securing the airway with adjunctive devices, by using a laryngeal mask airway (LMA), or by using a cuffed oropharyngeal airway (COPA). Each of these solutions has its respective drawbacks especially during procedures such as radiation treatment where deep anesthetization is not necessary, where the patient breathes by himself, and where treatment is on an on-going basis.

An endotracheal tube may be used to deliver anesthetic gases and to maintain a patient's airway. Endotracheal intubation is very stimulating because the endotracheal tube extends through the vocal chords and into the trachea. This requires that the patient be deeply anesthetized or partially paralyzed with neuromuscular blocking agents to keep him from reaction to the intubation. Thus, endotracheal intubation is not desirable for circumstances that do not require deep anesthetization. Endotracheal intubation also subjects the patient to laryngoscopy for inserting the endotracheal tube and to tracheal irritation which makes it undesirable for circumstances requiring repeated instrumentation. Generally, endotracheal intubation is better suited for more invasive procedures when the patient is deeply anesthetized and not responsive to the stimulation caused by the endotracheal tube and can not breathe on his own.

Intravenous techniques may obviate the use of inhalational agents, but still necessitate maintenance of a patent airway. Moreover, end-tidal carbon dioxide monitoring may be desirable in addition to supplemental oxygen during total intravenous anesthesia. Further, suction catheters must be introduced to suction secretions from the patient's pharynx.

An LMA may be used to provide oxygen to a patient and to monitor end-tidal carbon dioxide and is less invasive than an endotracheal tube because it does not go through the patient's vocal chords. However, the LMA must be connected to a conventional anesthesia circuit, does not provide a mechanism for suctioning secretions, and requires technical facility for its insertion that may require adjunctive equipment for its application. Further, the LMA is very stimulating because it includes a cuff that inflates in the patient's trachea to prevent reflux from the stomach from entering the trachea. This stimulation is undesirable in circumstances requiring repeated instrumentation.

A COPA is a device consisting of an airway with a cuff. A COPA device may be used to provide oxygen to a patient and to monitor end-tidal carbon dioxide. However, the COPA must be connected to a conventional anesthesia circuit or to an adapter to connect the COPA to an oxygen source and may cause the patient discomfort due to the inflated cuff. Further, the COPA does not include a suctioning mechanism which may result in a medical procedure being interrupted in order for an anesthesiologist to suction the patient when secretions are building up.

For the administration of anesthesia, there is a need for a device that will maintain a patent airway while providing the capability to oxygenate the patient, to provide suctioning, and to monitor end-tidal carbon dioxide. Further, there is a need for such a device that is minimally stimulating to allow for repeated use during on-going treatments, that does not block access to the face of a patient, and that allows an anesthesiologist to be distant from the patient.

SUMMARY OF THE INVENTION

The invention provides an oropharyngeal device for insertion into the mouth of a patient. The device includes a body having a distal end and a proximal end. The device body is sized such that when the distal end of the body is inserted into the mouth of the patient until the proximal end is disposed outside and adjacent to the patient's mouth, the distal end is disposed within the pharynx above the epiglottis. At least one channel extends between the proximal end and the distal end of the device body to form at least one airway in the device body. Inhalant gas may be conveyed to the patient via at least one first conduit that extends from the proximal end to the distal end of the device body. Suctioning may be applied via at least one second conduit that extends from the proximal end to the distal end of the device body. End-tidal carbon dioxide of gas exhaled by the patient may be monitored via at least one third conduit that extends from the proximal end of the device body and terminates at a position within the channel.

The invention also provides a method of establishing and maintaining an airway of a patient. The oropharyngeal device described above is inserted into the mouth of the patient until the proximal end is outside and adjacent to the patient's mouth. An inhalant gas source, a suctioning device, and a gas sampling device are connected to the first, second, and third conduits, respectively.

For purposes of illustrating the invention, the distal end of the device shall refer to the end which penetrates into the patient's airway (marked 106 in FIG. 1 and 206 in FIG. 2). The proximal end shall refer to the end which is held adjacent to the mouth (marked 104 in FIG. 1 and 204 in FIG. 2). The terms "proximal" and "distal" with respect to orientation and direction in the patient's airway shall mean, respectively, the directions toward and away from the patient's mouth.

BRIEF DESCRIPTION OF THE FIGURES

For the purpose of illustrating the invention, there is shown in the drawings a form that is presently preferred; it being understood, however, that this invention is not limited to the precise arrangements and instrumentalities shown.

FIG. 5A is an isometric view of an oropharyngeal device according to the present invention;

FIG. 5B is a cross-sectional view of the oropharyngeal device shown in FIG. 5A taken along line 5B-5B;

DETAILED DESCRIPTION OF THE INVENTION

Figure 1A:
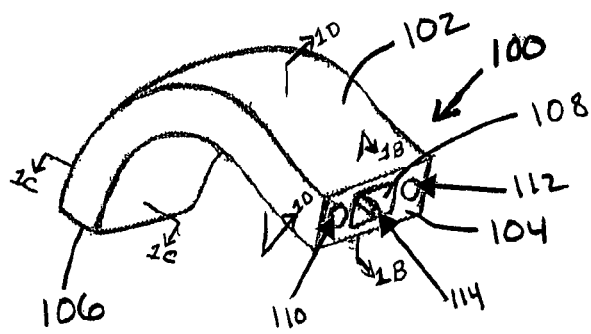
FIG. 1A is an isometric view of an oropharyngeal device according to the present invention.
Figure 1B:
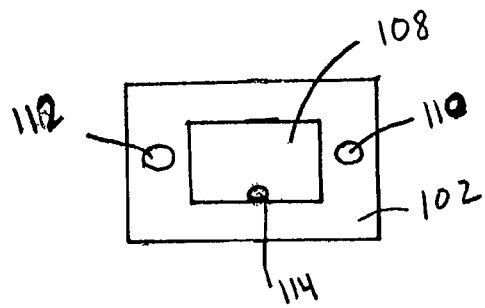
FIG. 1B is a cross-sectional view of the oropharyngeal device shown in FIG. 1A taken along line 1B-1B.
Figure 1C:
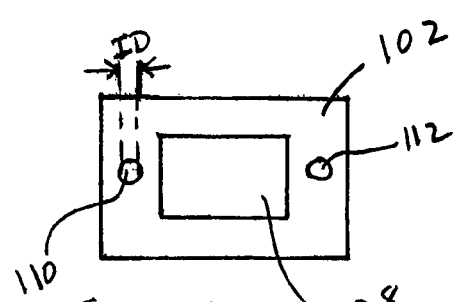
FIG. 1C is a cross-sectional view of the oropharyngeal device shown in FIG. 1A taken along line 1C-1C.
Figure 1D:
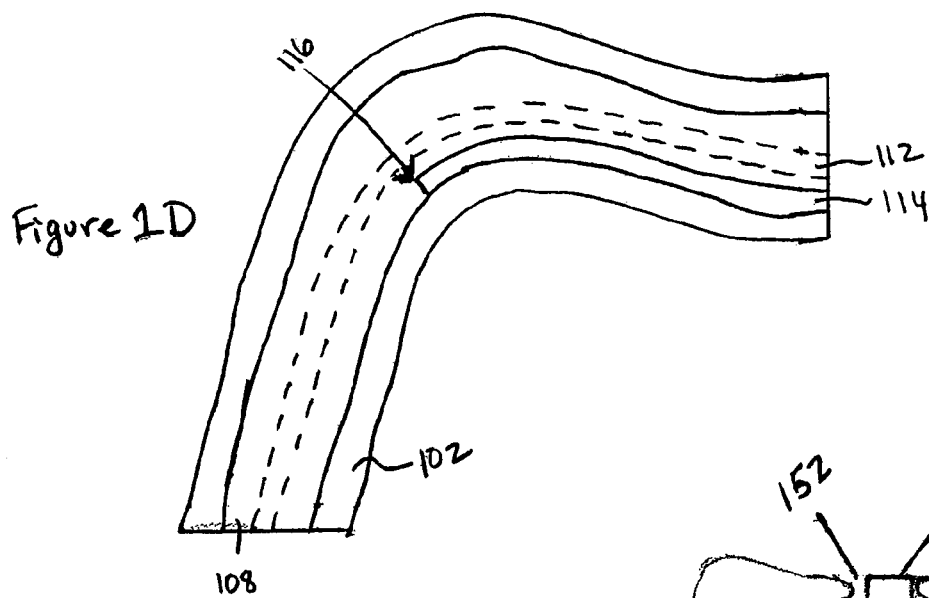
FIG. 1D is a cross-sectional view of the oropharyngeal device shown in FIG. 1A taken along line 1D-1D.

Referring to the drawings in which like reference numerals indicate like elements, there is shown in FIGS. 1A-E an oropharyngeal device 100 according to an exemplary embodiment of the present invention. The device 100 includes a body 102 having a proximal end 104 and a distal end 106.

Figure 1E:
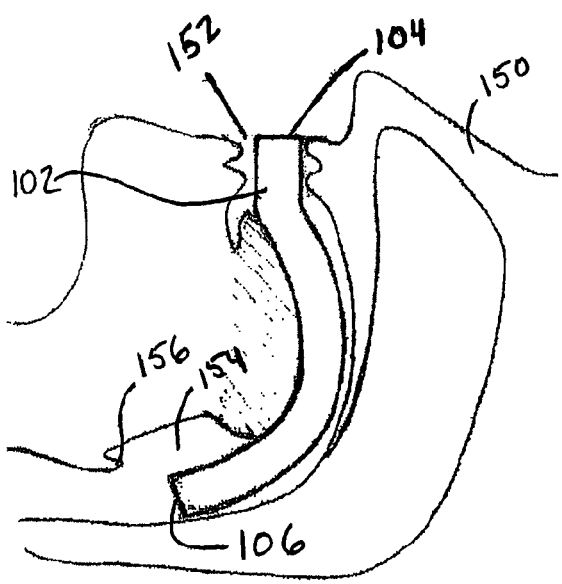
FIG. 1E is a sagittal view of a patient showing the oropharyngeal device of FIG. 1A inserted into the mouth of the patient.

A channel 108 forms an airway through the body 102 that extends through the body 102 from its proximal end 104 to its distal end 106. As illustrated in FIG. 1E, the body 102 is sized such that when the distal end 106 of the body 102 is inserted into the mouth 152 of a patient 150 until the proximal end 104 is disposed outside and adjacent to the patient's mouth 152, the distal end 106 of the body 102 is disposed within the pharynx 154 above the epiglottis 156. The body 102 may be formed of a rigid material to serve as a bite block to prevent the patient from biting any conduits inserted through the channel.

The airway channel may be completely enclosed within the body of the oropharyngeal device, as illustrated by channel 108, such that the airway channel has a closed cross section. Alternatively, one or more channels may be formed by a ridge, flange or protrusion running the length of the body, as illustrated by channels 508 and 509 in FIGS. 5A and 5B.

The device 100 includes three conduits 110, 112, 114 that may be used during the administration of anesthesia. The first conduit 110 is for conveying an inhaling gas to the patient 150. Conduit 110 extends from the proximal end 104 to the distal end 106 of the body 102. The second conduit 112 is for suctioning. It also extends from the proximal end 104 to the distal end 106 of the body 102. The third conduit 114 is for sampling gas exhaled by the patient 150. Conduit 114 extends in the channel 108 from the proximal end 104 of the body 102 and terminates at a position 116 in the channel 108. Conduit 114 extends to a position 116 within the channel 108 that corresponds to the location of the mouth of the patient 150, when the device is inserted.

Although the body 102 is illustrated in FIGS. 1A-E as having a rectangular closed cross-section, the body 102 may alternatively be formed in other shapes including a body having an oval, round or square-section. The channel 108 is also illustrated in FIGS. 1A-E as having a rectangular cross-section and may also be formed in other shapes, not necessarily the same shape as the body 102. Similarly, although the first, second, and third conduits 110, 112, 114 are illustrated as having round cross-sections, they too may be independently formed in other shapes.

In the embodiment illustrated in FIGS. 1A-E, the first and second conduits 110, 112, are formed within the body 102 and the third conduit 114 is formed within the channel 108. Alternatively, each conduit 110, 112, 114 may be formed either within the body 102, within the channel 108, or partially within the body 102 and partially within the channel 108. The first, second and third conduits each may have an internal diameter between 2 mm and 5 mm.

Figure 2A:
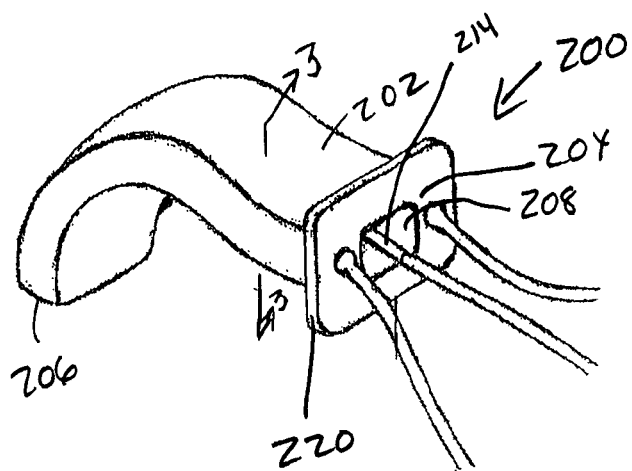
FIG. 2A is a front isometric view of an oropharyngeal device according to the present invention.
Figure 2C:
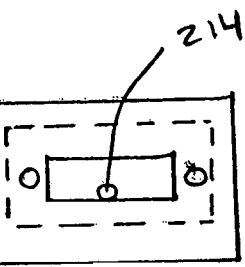
FIG. 2C is a front view of the proximal end of the oropharyngeal device shown in FIG. 2A without the conduits extending from the proximal end of the device.
Figure 2B:
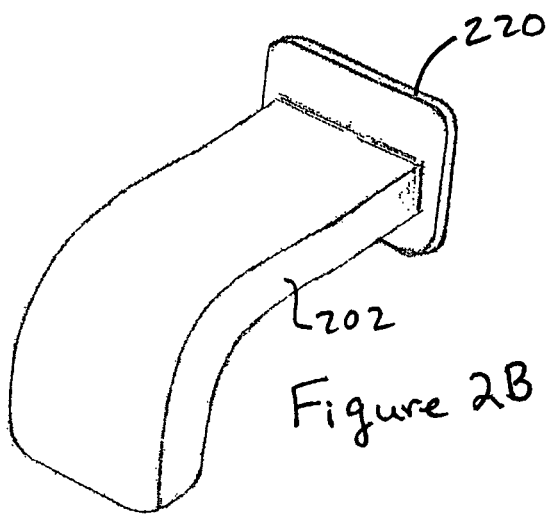
FIG. 2B is a rear isometric view of the oropharyngeal device shown in FIG. 2A.
Figure 2D:
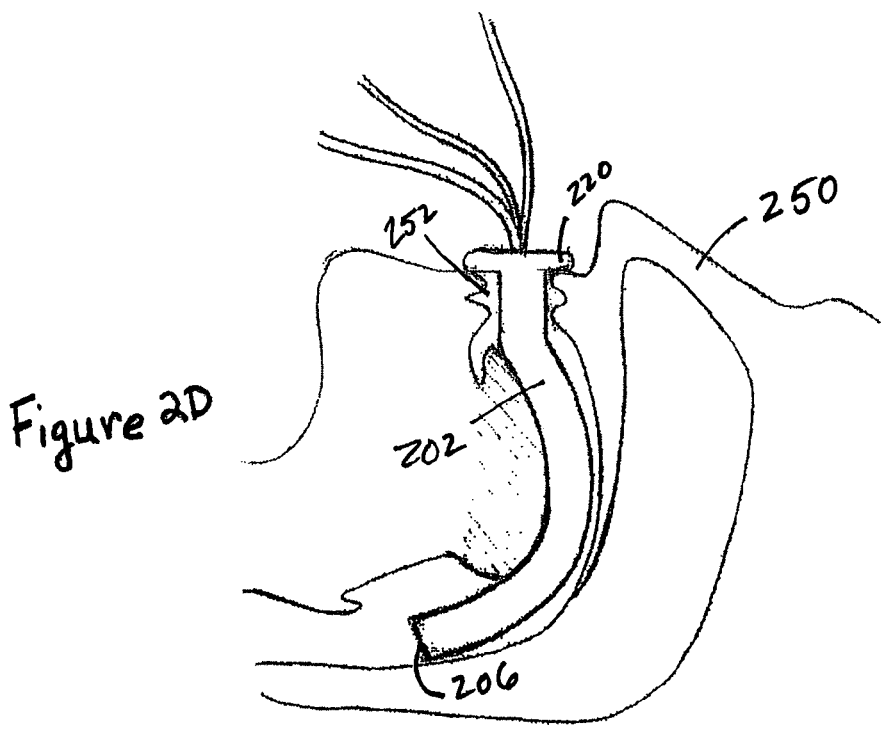
FIG. 2D is a sagittal view of a patient showing the oropharyngeal device of FIG. 2A inserted into the mouth of the patient.

A further embodiment of the oropharyngeal device of the invention is shown in FIGS. 2A-2D. The oropharyngeal device 200 includes a flange 220 at the proximal end 204 of the body 202. As illustrated in FIG. 2D, the distal end 206 of the body 202 is inserted into the mouth of a patient 250 such that the proximal end 204 of the body 202 is outside and adjacent to the patient's mouth 252. The flange 220 abuts the entrance of the patient's mouth and serves to prevent the oropharyngeal device 200 from further proceeding into the patient's mouth.

Figure 3A:
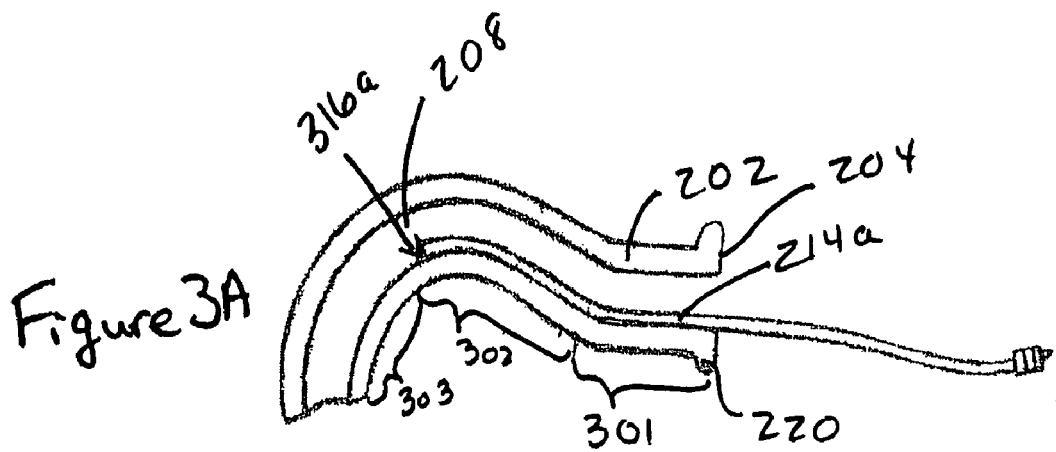
FIGS. 3A-3C are three cross-sectional views of the oropharyngeal device shown in FIG. 2A taken along line 3-3 in FIG. 2A illustrating three different lengths of the third conduit.
Figure 3B:
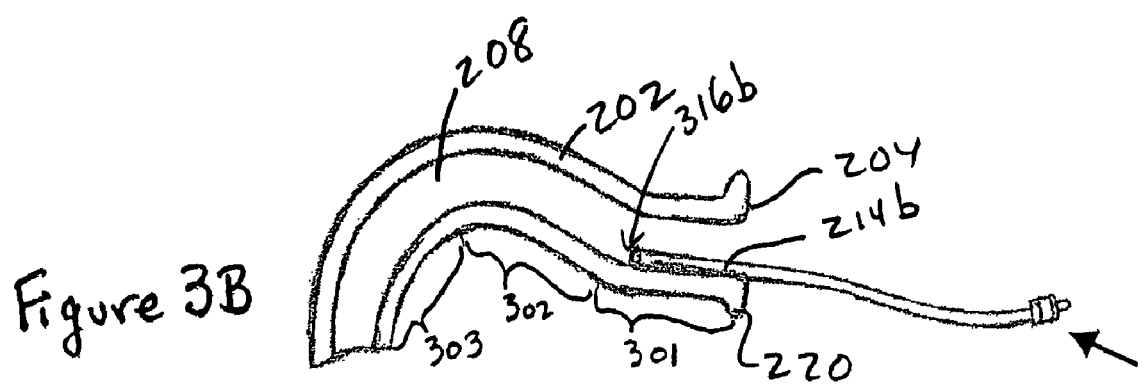
Figure 3C:
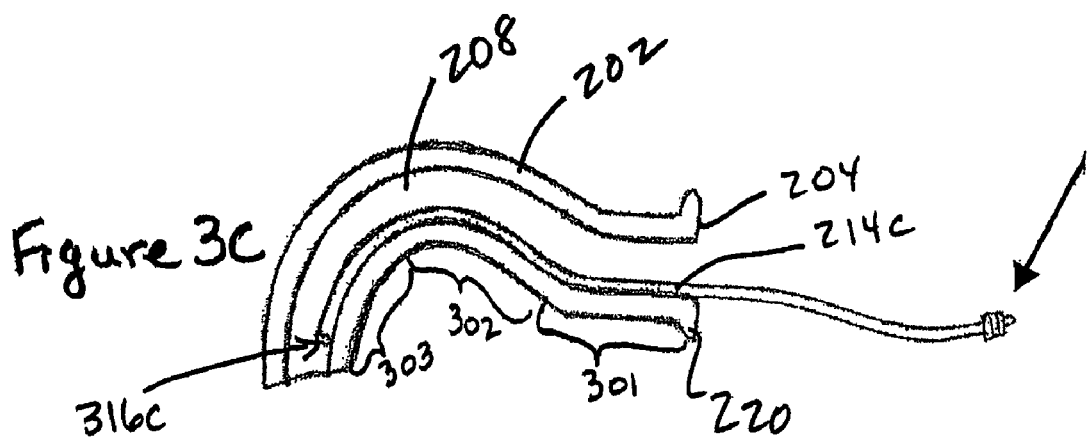

In certain embodiments of the invention, the third conduit 214 (for sampling patient exhaled gas) is contained in channel 208. In such embodiments, the third conduit 214 may terminate at various positions within the channel 208. FIGS. 3A-C are cross-sectional views of the oropharyngeal device 200 taken along line 3-3 in FIG. 2A which illustrate various positions within the channel 208 at which the third conduit 214 may terminate. Although end-tidal carbon dioxide is optimally monitored at the distal end 206 of the device body, a third conduit 214 having its distal end positioned at or terminating at the distal end 206 of the device body may be clogged by secretions. In FIG. 3A, the third conduit 214*a* extends from the proximal end 204 of the body 202 to a position 316*a* within the channel 208 located in the middle-third 302 of the body 202. In this central position 302, the third conduit 214*a* terminates at a position distant from the proximal end 204 for better gas sampling and at a position distant from the distal end 206 to avoid clogging. The third conduit 214*b* shown in FIG. 3B extends from the proximal end 204 of the body 202 to a position 316*b* within the channel 208 located within the first-third 301 of the body 202 as measured from the proximal end 204. The third conduit 214*c* shown in FIG. 3C extends from the proximal end 204 of the body 202*a* to a position 316*c* within the channel 208 located in the farthest-third 303 of the body 202 as measured from its proximal end 204.

Figure 4A:
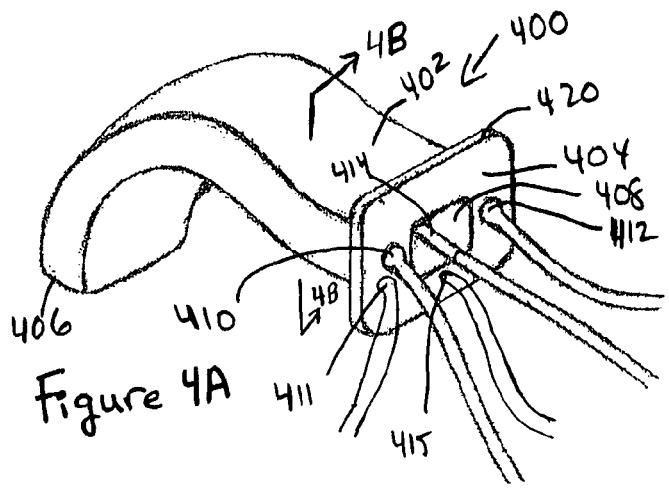
FIG. 4A is an isometric view of an oropharyngeal device according to the present invention.

The oropharyngeal device may include more than three conduits, where more than one inhalant gas conduit, suctioning conduit, or exhalation gas sampling conduit is present. The oropharyngeal device 400 shown in FIGS. 4A-C includes two conduits 410, 411 for administering an inhalant gas which may be used, for example, to separately administer two different inhalant gases or to administer a larger volume of a single inhalant gas. The oropharyngeal device 400 includes two conduits 414, 415 for sampling exhalant gas which may each be coupled, for example, to a different device for sampling different components of the exhalant gas. Alternatively, the second conduits 414, 415 may be used in a redundant fashion where one serves as the active conduit and the other serves as the standby conduit. In the event that the active conduit ceases to function as a result of clogging, for example, the standby conduit may instead be used to sample the exhalant gases.

Figure 4B:
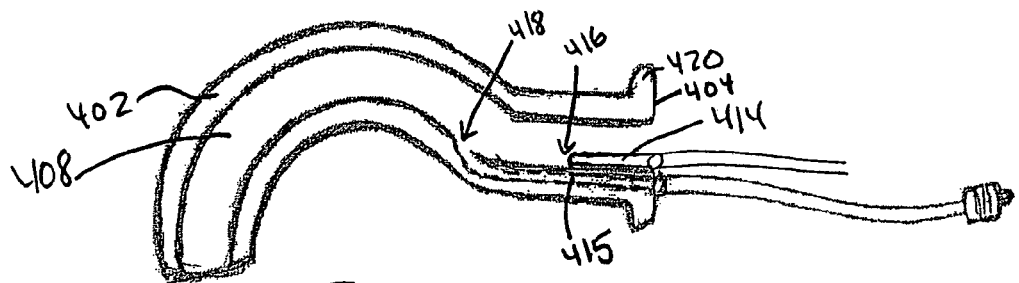
FIG. 4B is a cross-sectional view of the oropharyngeal device shown in FIG. 4A taken along line 4B-4B.
Figure 4C:
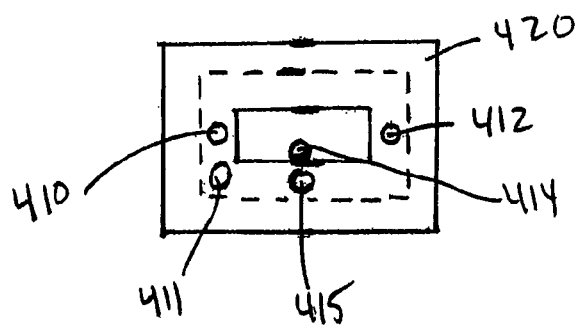
FIG. 4C is a front view of the proximal end of the oropharyngeal device shown in FIG. 4A without the conduits extending from the proximal end of the device.

As illustrated in FIG. 4B, the conduit 414 for sampling exhalant gases extends entirely within the channel 408 from the proximal end 404 of the body 402 to a position 416 where it terminates within the channel 408. The other conduit 415 for sampling exhalant gases is formed within the body 402 and extends from the proximal end 404 of the body 402 and terminates at a position 418 within the channel 408.

The present invention may be applied to oropharyngeal devices having bodies of various shapes. For example, the oropharyngeal device 500 shown in FIG. 5A includes two U-shaped channels 508, 509 formed within a body 502 having an I-shaped cross-section.

The oropharyngeal device 500 includes a first conduit 510 for administrating an inhalant gas that extends through the body 502 from its proximal end 504 to its distal end 506. A second conduit 512 for suctioning also extends through the body 502 from its proximal end 504 to its distal end 506. A third conduit 514 for sampling exhalant gases is formed adjacent to a sidewall 520 of the channel 509 and extends from the proximal end 504 of the body 502 to a position 516 within the channel 509.

Figure 6A:
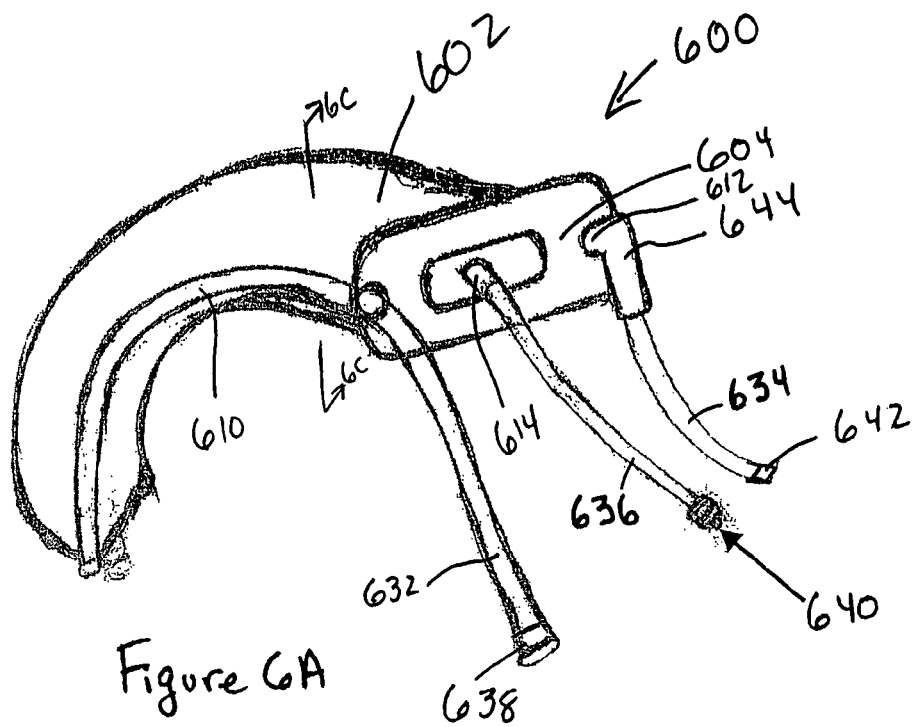
FIG. 6A is an isometric view of an oropharyngeal device according to the present invention.
Figure 6C:
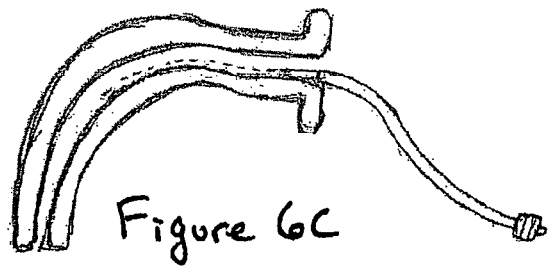
FIG. 6C is a cross-sectional view of the oropharyngeal device shown in FIG. 6A taken along line 6C-6C.
Figure 6B:
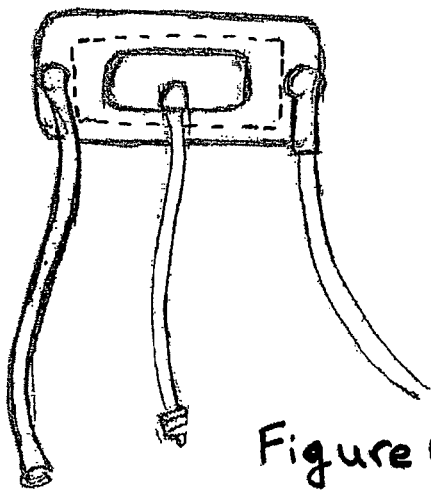
FIG. 6B is a front view of the proximal end of the oropharyngeal device shown in FIG. 6A.

To facilitate connection and disconnection of conventional devices such as inhalant gas sources, gas sampling devices, and suctioning devices to the conduits of an oropharyngeal device according to the present invention, the oropharyngeal device may include standard connectors for connecting to such devices. The connectors may be connected to the first, second, and third conduits at the proximal end of the body. Alternatively, as shown in FIGS. 6A-C, the oropharyngeal device 600 may include flexible hoses, 632, 634, 636 coupled to the ends of the first, second, and third conduits 610, 612, 614, respectively, at the proximal end 604 of the body 602. The ends of the flexible hoses 632, 634, 636 may include connectors 638, 640, 642.

During some medical procedures the mouth of the patient may be covered and it may be desirable for the hoses 632, 634, 636 or connections to other devices be coupled to the oropharyngeal device 600 from the side. In such cases, a right-angle connector 644 may be used to connect a conduit 612 to the hose 634. Alternatively, instead of the conduits 610, 612, 614 extending to the proximal end 604 of the body 602, the conduits may exit a side of the body 602 adjacent to the proximal end 604 or may exit through the side of the flange.

An oropharyngeal device according to the present invention allows for maintenance of an airway while simultaneously administering an inhalant gas, suctioning, and sampling an exhalant gas. This is possible without obstructing access to the face of a patient because first, second, and third conduits for each purpose are integrated into the device. This facilitates the administration of anesthesia during treatment of a patient's head or neck despite lack of or obstructed access to the patient's mouth, face, or airway. In the event that mechanical ventilation or "positive pressure" is required to augment a patient's breathing while an oropharyngeal device according to the present invention is in use, a mask for providing mechanical ventilation may be applied over the device and the patient's mouth.

The oropharyngeal device is sized to terminate above or proximal to the path of travel of the epiglottis and avoids manipulation of the larynx and subglottic structures. This avoids increased stimulation and avoids medical complications associated with devices which may impinge on or cause damage to the delicate laryngeal and supra-laryngeal structures and makes the oropharyngeal device suitable for circumstances requiring repeated use such as during on-going radiation treatment. A patient may be taken to a recovery area with the oropharyngeal device still in position and it can then be easily removed as the patient awakens, with very little discomfort to the mouth or throat.

The oropharyngeal device may be inserted in a similar fashion to conventional oropharyngeal airways and thus is simple to apply, does not require extensive training or instruction to use, and does not require any special or additional equipment such as an anesthesia circuit. Further, the device is recognizable as an anesthesia device and will be readily acceptable to anesthesia personnel. The device may be used to assist in the placement of an endotracheal tube by inserting a fiber optic scope device in the channel for placing the endotracheal device through or adjacent to the oropharyngeal device.

All documents referred to herein are incorporated by reference. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

We claim:

1. An oropharyngeal device for maintaining a patient airway without requiring endotracheal intubation, a laryngeal mask or a cuffed airway, wherein the device is adapted for insertion through the mouth of a patient and with one end into the pharynx of a patient above and spaced from the epiglottis of the patient, and which allows an administering anesthesiologist to be distant from the patient during use, comprising:

a. a body having a distal end and a proximal end, the body sized such that when the distal end of the body is inserted into the mouth of the patient until the proximal end is disposed outside and adjacent to the patient's mouth, wherein in a fully deployed state, the distal end is disposed within the pharynx above the epiglottis and at a distance from the epiglottis;

b. at least one channel forming at least one airway in the device body extending between the proximal end and the distal end of the device body, wherein the channel has a proximate end and a distal end and the channel being sized to comprise connection means whereby, when, in a fully deployed state, the distal end is disposed within the pharynx above the epiglottis and at a distance from the epiglottis;

c. at least one first conduit in the device body for conveying an inhalant gas to the patient, that extends from the proximal end to the distal end of the device body, and said at least one first conduit including connection means at a proximal end of the device for providing inhalant gas, with the at least one first conduit having a proximal end and a distal end, wherein the at least one first conduit in its fully deployed state with connection means at its proximal end, has its distal end disposed within the pharynx above the epiglottis and at a distance from the epiglottis;

d. at least one second conduit for suctioning that extends from the proximal end to the distal end of the device body and said at least one second conduit including connection means at a proximal end of the device for suction, wherein the at least one second conduit has a proximal end and a distal end, wherein the at least one second conduit in its fully deployed state, with connection means at its proximal end, has its distal end disposed within the pharynx above the epiglottis and at a distance from the epiglottis;

e. at least one third conduit for sampling gas exhaled by the patient that extends from the proximal end of the device body and terminates at a position in the channel, and said at least one third conduit including connection means at a proximal end of the device for withdrawing sampling gas, wherein the at least one third conduit has a proximal end and a distal end, and with the at least one third conduit in its fully deployed state, with connection means at its proximal end, has its distal end disposed above the epiglottis and at a distance from the epiglottis;

f. whereby the sizing of the device and its channel and conduits to terminate above the epiglottis and at a distance from the epiglottis avoids manipulation of the larynx and subglottic structures during use; and g. wherein the first, second and third conduits comprise connection means whereby administration of inhalant gas, suctioning and the sampling of gas exhaled by the patient may take place simultaneously through separate conduits.

2. The oropharyngeal device according to claim 1 wherein the at least one first, second, and third conduits is disposed within the device body.

3. The oropharyngeal device according to claim 1 wherein the at least one first, second, and third conduits are independently disposed within the at least one channel.

4. The oropharyngeal device according to claim 1 wherein the at least one first, second, and third conduits are independently disposed partly within the device body and partly within the at least one channel.

5. The oropharyngeal device according to claim 1 wherein the third conduit terminates at a position within the channel corresponding to the mouth of the patient.

6. The oropharyngeal device according to claim 1 wherein the device body has a length from its proximal end to its distal end and the at least one third conduit terminates within the channel at a location within the two-thirds of the device body length closest to the proximal end of the device body.

7. The oropharyngeal device according to claim 1 wherein the at least one channel has a U-shaped cross section.

8. The oropharyngeal device according to claim 1 wherein the at least one channel has a closed cross section.

9. The oropharyngeal device according to claim 1 wherein the device is rigid and functions as a bite block.

10. The oropharyngeal device according to claim 1 wherein the first, second, and third conduits each independently have an inside diameter between 2 mm and 5 mm.

11. The oropharyngeal device according to claim 1 further comprising at least one flexible extension conduit coupled to at least one of the first, second, and third conduits at the proximal end of the device body.

12. The oropharyngeal device according to claim 1 further comprising a flange at the proximal end of the device for preventing the proximal end of the device body from entering the mouth.

13. The oropharyngeal device according to claim 1 further comprising at least one right-angled connector coupled to at least one of the first, second, and third conduits at the proximal end of the device wherein the right-angled connector bends at a right mule with respect to a surface of the device body at its proximal end.

14. The oropharyngeal device according to claim 6 wherein the at least one channel has a closed cross section, the at least one first conduit is disposed within the device body, and the at least one second conduit is disposed within the device body.

15. A method for establishing and maintaining an airway comprising the steps of:

a. inserting the device according to claim 1 into the mouth of the patient until the proximal end is outside of an adjacent to the patient's mouth;

b. connecting at least one inhalant gas source to the at least one first conduit;

c. connecting at least one suctioning device to the at least one second conduit; and d. connecting at least one gas sampling device to the at least one third conduit.

* * * * *

UNITED STATES PATENT AND TRADEMARK OFFICE
CERTIFICATE OF CORRECTION

PATENT NO. : 7,278,420 B2  Page 1 of 1
APPLICATION NO. : 10/666290
DATED : October 9, 2007
INVENTOR(S) : Arjunan Ganesh, Valerie E. Armstead and Michael J. Williams It is certified that error appears in the above-identified patent and that said Letters Patent is hereby corrected as shown below:

Column 8, line 42, delete "mule" and insert --angle--

Signed and Sealed this

Fifteenth Day of April, 2008

JON W. DUDAS
*Director of the United States Patent and Trademark Office*